(12) United States Patent
Leber et al.

(10) Patent No.: US 7,166,624 B2
(45) Date of Patent: Jan. 23, 2007

(54) PEPTIDE DEFORMYLASE INHIBITORS

(75) Inventors: Jack Dale Leber, Collegeville, PA (US); Mei Li, Collegeville, PA (US); Jinhwa Lee, Collegeville, PA (US); Kelly M. Aubart, Collegeville, PA (US); Siegfried B. Christensen, IV, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/539,674

(22) PCT Filed: Dec. 18, 2003

(86) PCT No.: PCT/US03/40763

§ 371 (c)(1),
(2), (4) Date: Jun. 16, 2005

(87) PCT Pub. No.: WO2005/032550

PCT Pub. Date: Apr. 14, 2005

(65) Prior Publication Data

US 2006/0052423 A1    Mar. 9, 2006

Related U.S. Application Data

(60) Provisional application No. 60/434,466, filed on Dec. 18, 2002.

(51) Int. Cl.
*A61K 31/4245*    (2006.01)
*C07D 271/10*    (2006.01)
*C07D 271/113*    (2006.01)

(52) U.S. Cl. .................. 514/364; 548/143; 548/144

(58) Field of Classification Search ................ 548/143, 548/144; 514/364
See application file for complete search history.

(56) References Cited

U.S. PATENT DOCUMENTS 3,502,668 A    3/1970    Palazzo et al. .......... 260/247.5

*Primary Examiner*—Laura L. Stockton
(74) *Attorney, Agent, or Firm*—Laura K. Madden; Loretta J. Sauermelch; Mary E. McCarthy

(57) ABSTRACT

Novel PDF inhibitors and novel methods for their use are provided.

8 Claims, 1 Drawing Sheet

PEPTIDE DEFORMYLASE INHIBITORS

This application is a 371 of International Application No. PCT/US2003/040763, filed 18 Dec. 2003, which claims priority of U.S. Provisional Application No. 60/434,466, filed 18 Dec. 2002.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formylmethionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1).

To date, polypeptide deformylase homologous genes have been found in bacteria, in chloroplast-containing plants, in mice and in human. The plant proteins are nuclear encoded but appear to carry a chloroplast localization signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165–168, 2000).

Polypeptide deformylase is found in all eubacteria for which high coverage genomic sequence information is available. Sequence diversity among PDF homologs is high; with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749–761, 1997).

PDF is recognized to be an attractive antibacterial target, as this enzyme has been demonstrated to be essential for bacterial growth in vitro (Mazel, D. et al., EMBO J. 13 (4), 914–923, 1994), is not believed to be involved in eukaryotic protein synthesis (Rajagopalan et al., J. Am. Chem. Soc. 119, 12418–12419, 1997), and is universally conserved in prokaryotes (Kozak, M., Microbiol. Rev. 47, 145, 1983). Therefore PDF inhibitors can potentially serve as broad-spectrum antibacterial agents.

SUMMARY OF THE INVENTION

The present invention involves novel anti-bacterial compounds represented by Formula (1) hereinbelow and their use as PDF inhibitors.

DETAILED DESCRIPTION OF THE INVENTION

Figure 1:
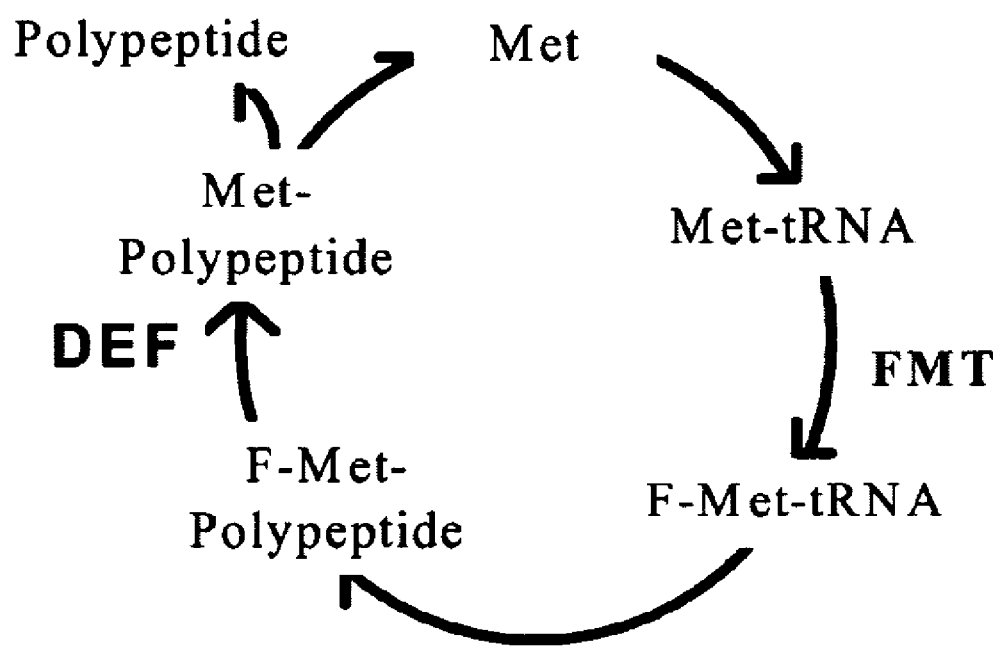
FIG. 1: Provides a graph of the methionine cycle.

In one aspect of the present invention, there is provided a compound of formula (1):

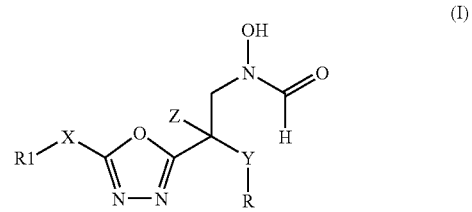

wherein:

X is selected from the group consisting of $CH_2$, $NR_2$, O, $NR_2CO$, $CONR_2$ and a bond;

Y represents O, $CH_2$ or a bond:

Z represents H or F;

R is selected from the group consisting of:
  $C_{2-6}$ alkyl optionally substituted by alkoxy, halogen, or $C_{1-3}$ alkylsulfanyl, $C_{2-6}$ alkenyl optionally substituted by alkoxy, halogen, or $C_{1-3}$ alkylsulfanyl, $C_{2-6}$ alkynyl optionally substituted by alkoxy, halogen, or $C_{1-3}$ alkylsulfanyl, $(CH_2)_n$—$C_{3-6}$ carbocycle optionally substituted by alkoxy, halogen, or $C_{1-3}$ alkylsulfanyl, $(CH_2)_n$—R3 {wherein R3 is phenyl, furan, benzofuran, thiophene, benzothiophene, tetrahydrofuran, tetrahydropyran, dioxane, 1,4-benzodioxane or benzo[1,3]dioxole; such that R3 is optionally substituted by one or more Cl, Br, I, $C_{1-3}$ alkyl (optionally substituted by one to three F, or $C_{1-2}$, alkoxy optionally substituted by one to three F};

R1 is selected from the group consisting of:
  hydrogen, $C_{1-3}$ substituted alkyl, $C_{2-3}$ substituted alkenyl, $C_{2-3}$ substituted alkynyl, $(CH_2)_n$—$C_{3-6}$ substituted carbocycle, aryl, heteroaryl, heterocyclic, and aminocarbonyl; provided that X is $(CH_2)_n$ when R1 represents aminocarbonyl.

R2 represents:
  hydrogen, or $C_{1-3}$ substituted alkyl;

X represents $(CH_2)_n$, NR2, O, NR2CO, CONR2 or a bond;

Y represents O, $CH_2$ or a covalent bond;

Z represents hydrogen or fluorine; preferably fluorine; and n represents an integer between 0 and 2 or a salt, solvate, or physiologically functional derivative thereof.

In this invention the most preferred absolute configuration of compounds of the formula (1) is indicated below:

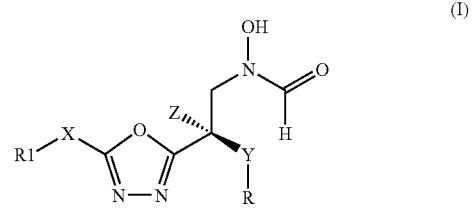

wherein:

X is selected from the group consisting of $CH_2$, $NR_2$, O, $NR_2CO$, $CONR_2$ and a bond;

Y represents O, $CH_2$ or a bond:

Z represents H or F;

In a second aspect of the present invention, there is provided a compound of Formula (1) wherein $X=CH_2$ or a bond, and R, R1, R2, R3, Y, Z and n are as defined above; or a salt, solvate, or physiologically functional derivative thereof.

In a third aspect of the present invention, there is provided a compound of Formula (1) wherein $X=NR2$, and R, R1, Y, Z and n are as defined above; or a salt, solvate, or physiologically functional derivative thereof.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, hexyl and the like.

As used herein, the term "substituted alkyl" refers to a straight or branched chain saturated hydrocarbon radical, optionally substituted with substituents selected from the group that includes $C_{1-3}$ alkyl (optionally substituted by one to three fluorines), $C_{2-3}$ alkenyl, $C_{2-3}$ alkynyl, $C_{1-2}$ alkoxy (optionally substituted by one to three fluorines), sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen, multiple degrees of substitution being allowed.

As used herein, the term "alkenyl" refers to a straight or branched chain hydrocarbon radical having at least one carbon—carbon double bond. Examples of "alkenyl" as used herein include, but are not limited to, ethenyl and propenyl.

As used herein, the term "substituted alkenyl" refers to a straight or branched chain hydrocarbon radical having at least one carbon—carbon double bond, optionally substituted with substituents selected from the group which includes $C_{1-3}$ alkyl (optionally substituted by one to three F), amino, aryl, cyano and halogen, multiple degrees of substitution being allowed.

As used herein, the term "alkynyl" refers to a straight or branched chain hydrocarbon radical having at least one carbon—carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon—carbon triple bond, optionally substituted with substituents selected from the group which includes $C_{1-3}$ alkyl (optionally substituted by one to three F), amino, aryl and halogen, multiple degrees of substitution being allowed.

As used herein, the term "halogen" refers to fluorine (F), chlorine (Cl), bromine (Br), or iodine (I), and "halo" refers to the halogen radicals fluoro, chloro, bromo and iodo.

As used herein, the term "carbocycle" refers to a non-aromatic cyclic hydrocarbon radical having from three to seven carbon atoms. For carbocycles with five- to seven-membered rings, a ring double bond is allowed. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical having from three to seven carbon atoms, and which is optionally substituted with substituents selected from the group which includes $C_{1-3}$ alkyl (optionally substituted by one to three F), $C_{2-3}$ alkenyl, $C_{2-3}$ alkynyl, $C_{1-2}$ alkoxy (optionally substituted by one to three F), sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen, multiple degrees of substitution being allowed. For carbocycles with five- to seven-membered rings, a ring double bond is allowed.

As used herein, the term "aryl" refers to an optionally substituted benzene ring or to an optionally substituted benzene ring fused to one or more optionally substituted benzene rings to form a ring system. Exemplary optional substituents include $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring or ring system may be optionally fused to one or more optionally substituted aryl rings (including benzene rings), carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six membered aromatic ring containing one or more heteroatomic substitutions selected from S, SO, $SO_2$, O, N, or N-oxide, or to such an aromatic ring fused to one or more optionally substituted rings, such as heteroaryl rings, aryl rings, heterocyclic rings, or carbocycle rings (e.g., a bicyclic or tricyclic ring system). Examples of optional substituents are selected from the group which includes $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido, multiple degrees of substitution being allowed. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with substituents selected from the group which includes $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring can be saturated or have one or more degrees of unsaturation. Such a ring may be optionally fused to one or more other optionally substituted "heterocyclic" ring(s), aryl ring(s), heteroaryl ring(s), or carbocycle ring(s). Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]-dioxonyl, 2,2-difluorobenzo-[1,3]-dioxonyl, 2,3-dihydro-phthalazine-1,4-dionyl, isoindole-1,3-dionyl, and the like.

As used herein, the term "alkoxy" refers to the group —OR$_a$, where R$_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy, and t-butoxy.

As used herein the term "aralkoxy" refers to the group —OR$_a$R$_b$, where R$_a$ is alkyl and R$_b$ is aryl as defined above.

As used herein the term "aryloxy" refers to the group —OR$_a$, where R$_a$ is aryl as defined above.

As used herein, the term "mercapto" refers to the group —SH.

As used herein, the term "sulfanyl" refers to the group —SR$_a$, where R$_a$ is substituted alkyl, substituted carbocycle, aryl, heteroaryl or heterocyclic, as defined above.

As used herein, the term "sulfinyl" refers to the group —S(O)R$_a$, where R$_a$ is substituted alkyl, substituted carbocycle, aryl, heteroaryl or heterocyclic, as defined above.

As used herein, the term "sulfonyl" refers to the group —S(O)$_2$R$_a$, where R$_a$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —NH$_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —S(O)$_2$NH$_2$. The aminosulfonyl group is optionally substituted by substituted alkyl, substituted carbocycle, aryl, heteroaryl or heterocyclic, as defined above.

As used herein, the term "sulfonylamino" refers to the group —NHS(O)$_2$R$_a$ where R$_a$ is substituted alkyl, substituted carbocycle, aryl, heteroaryl or heterocyclic, as defined above.

As used herein, the term "carboxyamide" refers to the group —NHC(O)R$_a$ where R$_a$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —C(O)NH$_2$. The aminocarbonyl group is optionally substituted by substituted alkyl, substituted carbocycle, aryl, heteroaryl or heterocyclic, as defined above.

As used herein, the term "ureido" refers to the group —NHC(O)NHR$_a$ wherein R$_a$ is hydrogen, alkyl, carbocycle or aryl as defined above.

As used herein, the term "guanidino" refers to the group —NHC(=NH)NH$_2$.

As used herein, the term "acyl" refers to the group —C(O)R$_a$, where R$_a$ is alkyl, carbocycle, or heterocyclic as defined herein.

As used herein, the term "aroyl" refers to the group —C(O)R$_a$, where R$_a$ is aryl as defined herein.

As used herein, the term "heteroaroyl" refers to the group —C(O)R$_a$, where R$_a$ is heteroaryl as defined herein.

As used herein, the term "acyloxy" refers to the group —OC(O)R$_a$, where R$_a$ is alkyl, carbocycle, or heterocyclic as defined herein.

As used herein, the term "aroyloxy" refers to the group —OC(O)R$_a$, where R$_a$ is aryl as defined herein.

As used herein, the term "heteroaroyloxy" refers to the group —OC(O)R$_a$, where R$_a$ is heteroaryl as defined herein.

Also included in the present invention are pharmaceutically acceptable salts and complexes, such as the hydrochloride, hydrobromide and trifluoroacetate salts and the sodium, potassium and magnesium salts. The compounds of the present invention may contain one or more asymmetric carbon atoms and may exist in racemic and optically active forms. All of these compounds and diastereomers are contemplated to be within the scope of the present invention.

General Synthetic Sequence

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of Formula (1) that can be prepared from the common racemic intermediate (8), or common chiral intermediates (17) and (25).

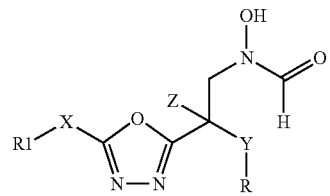

(1) X=CH2, NR$_2$, O, NR2CO, CONR2 or a bond; Y=O, CH$_2$ or a bond; Z=H or F

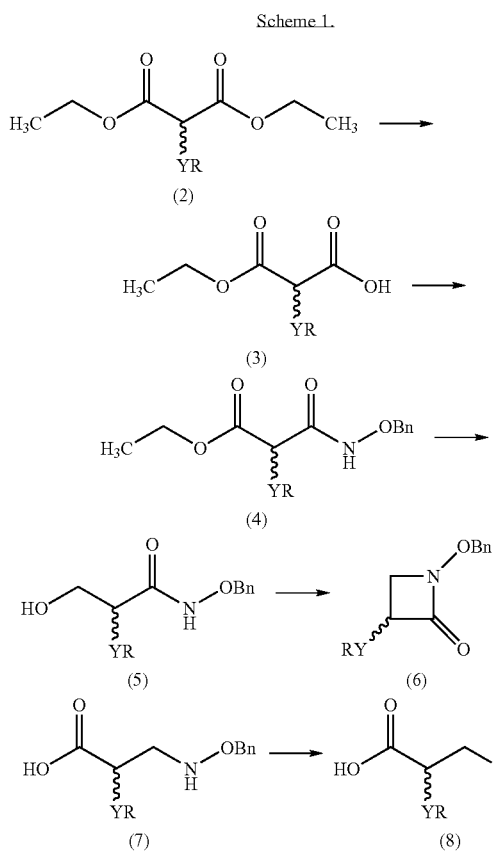

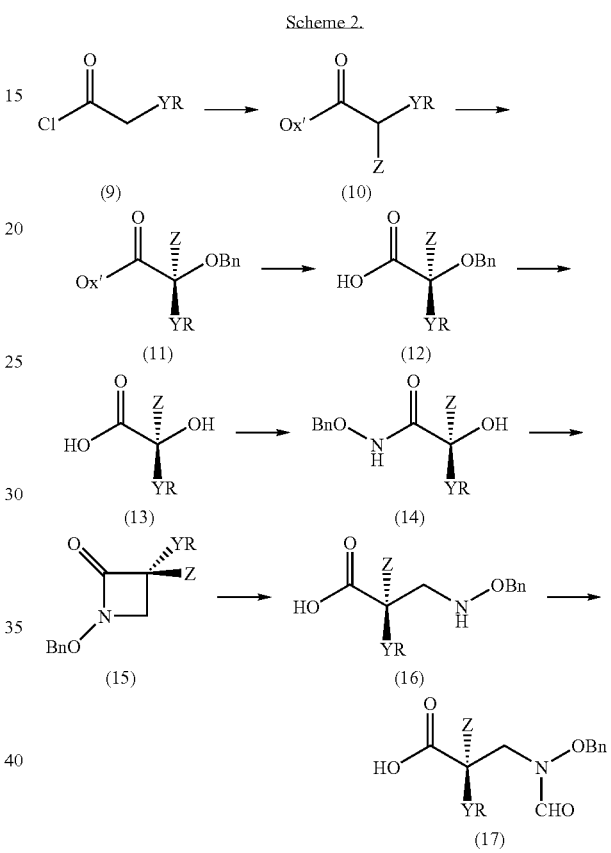

As shown in Scheme 1, intermediate (8) can be prepared by reacting the mono-substituted dialkyl malonate (2) with a base, such as potassium hydroxide, in an appropriate solvent, such as ethanol/water, to afford the mono-acid (3). Coupling of (3) with O-benzylhydroxylamine in the presence of a coupling reagent, such as 1-[3-(dimethylamino)propyl]-3-ethylcarbodiimide hydrochloride (EDCI), and a base, such as 4-dimethylaminopyridine, (DMAP) in an appropriate solvent, such as dichloromethane, gives the amide (4). Reduction of the ester functionality of compound (4) with a reducing agent, such as lithium borohydride, in an appropriate solvent, such as tetrahydrofuran, at room temperature provides the alcohol (5). Treatment of the alcohol (5) under Mitsunobu conditions affords the lactam (6). The same transformation may be achieved by treating (5) with triphenylphosphine, carbon tetrachloride and a base, such as triethylamine, to obtain (6). Hydrolysis of the lactam (6) using, for example, lithium hydroxide in an appropriate solvent mixture, such as THF—H₂O-MeOH, gives acid (7). Formylation of the amine group of (7) is achieved using formic acid and acetic anhydride in a solvent, such as dichloromethane, to provide the formylated compound (8).

Any racemates can be resolved at the level of any intermediate during the synthesis or at the level of the final product using, for example, a chiral chromatography method, to provide compound (8) in each of two enantiomeric forms.

Alternatively, an enantiomer of intermediate (8), such as (17) in Scheme 2 or (25) in Scheme 3, can be prepared by reacting an appropriate acid chloride (9) with a chiral agent, such as Evans' chiral oxazolidinone, in the presence of a base, such as n-butyl lithium, to afford the chiral intermediate (10) in Scheme 2 or (18) in Scheme 3. Treatment of the compound (10) or (18) with a base, such as diisopropylethylamine, in the presence of a chelating agent, such as titanium tetrachloride, in a solvent, such as tetrahydrofuran, followed by addition of an electrophile, such as benzyloxymethylchloride, provides either of two chiral compounds (11) and (19), depending on the selection of chiral auxiliary.

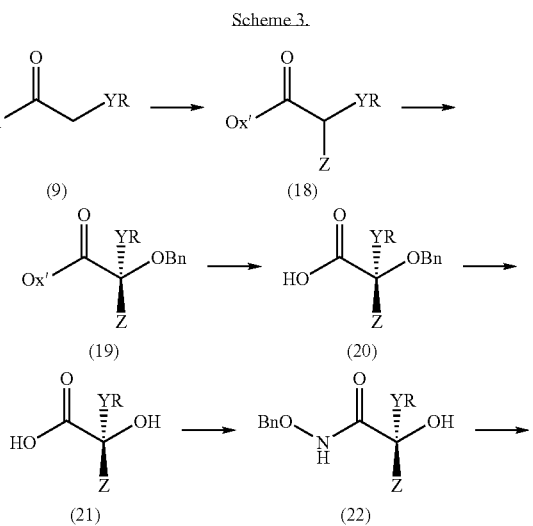

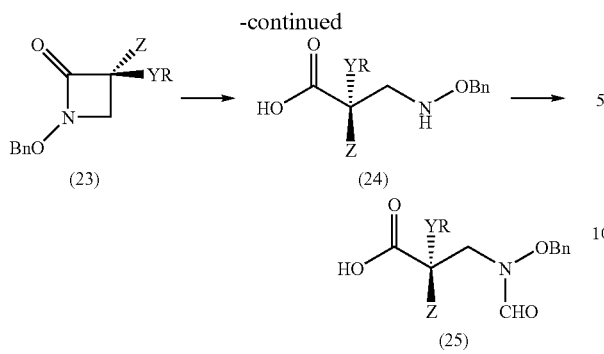

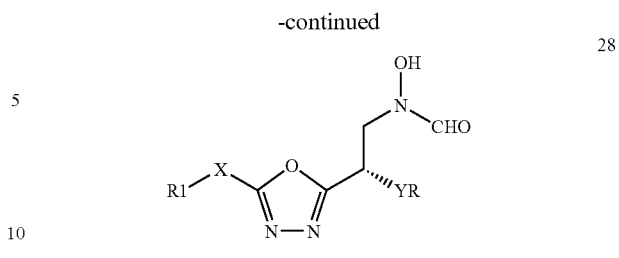

Conversion of compound (11) or (19) to the corresponding hydroxyacid (13) or (21) can be achieved by a sequence comprising oxidative cleavage of the chiral oxazolidinone, using, for example, $H_2O_2$ and lithium hydroxide to the respective intermediates (12) and (20), followed by hydrogenolysis. Coupling of the acid (13) or (21) with benzyloxyamine in the presence of coupling agents, such as EDCI/DMAP, yields the amides (14) and (22). These can be cyclized to the azetidin-2-ones (15) or (23) using either Mitsunobu conditions or a combination of triphenylphosphine/carbon tetrachloride/triethylamine. Hydrolysis of the azetidin-2-one (15) or (23), using for example lithium hydroxide, in an appropriate solvent, gives the corresponding acid (16) or (24). Conversion of compound (16) or (24) to the formate (17) or (25) can be achieved using an appropriate formylating agent, such as formic acid/acetic anhydride or methyl formate, in an appropriate solvent, such as dichloromethane.

Preparation of compound (10) or (18) Z=fluorine can be accomplished using the method of Franklin A. Davis, Vaidyanathan Srirajan, and Donald D. Titus *J. Org. Chem.* 1999, 64, 6931–6934.

SPECIFIC EMBODIMENTS

Second Embodiment

As the second embodiment of the present invention, the compounds of Formula (1) with X=CH$_2$ or a bond are disclosed, as in the racemic compound (26) and the chiral compounds (27) and (28).

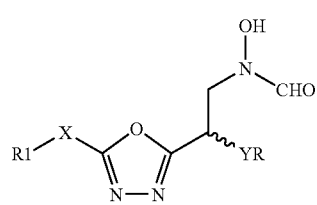

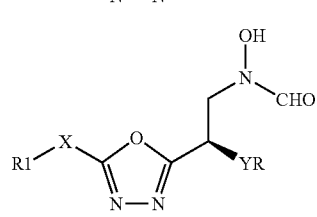

Preferred compounds useful in the present invention are selected from the group consisting of:

N-[(R)-2-(5-Benzo[1,3]dioxol-5-yl-[1,3,4]oxadiazol-2-yl)-heptyl]-N-hydroxyformamide;
N-[(R)-2-(5-Benzyl-[1,3,4]oxadiazol-2-yl)-heptyl]-N-hydroxyformamide;
N-Hydroxy-N-{(R)-2-[5-(7-methoxy-benzofuran-2-yl)-[1,3,4]oxadiazol-2-yl]-heptyl}-formamide;
N-Hydroxy-N-{(R)-2-[5-(1,2,3,4-tetrahydroquinolin-6-yl)-[1,3,4]oxadiazol-2-yl]-heptyl}-formamide;
N-Hydroxy-N-{(R)-2-[5-(1,2,3,4-tetrahydro-quinolin-8-yl)-[1,3,4]oxadiazol-2-yl]heptyl}-formamide;
N-Hydroxy-N-[(R)-2-(5-pyridin-3-ylmethyl-[1,3,4]oxadiazol-2-yl)-heptyl]-formamide;
N-{(R)-2-[5-(3,4-Dichloro-benzyl)-[1,3,4]oxadiazol-2-yl]-heptyl}-N-hydroxy-formamide;
N-{(R)-2-[5-(3,4-Dichloro-benzyl)-[1,3,4]oxadiazol-2-yl]-heptyl}-N-hydroxy-formamide;
N-{(R)-2-[5-(3,4-Dichloro-benzyl)-[1,3,4]oxadiazol-2-yl]-heptyl}-N-hydroxy-formamide;
N-Hydroxy-N-{(R)-2-[5-(2-morpholin-4-yl-ethyl)-[1,3,4]oxadiazol-2-yl]-heptyl}-formamide;
N-Hydroxy-N-{(R)-2-[5-(2-morpholin-4-yl-ethyl)-[1,3,4]oxadiazol-2-yl]-heptyl}-formamide;
N-{(R)-2-[5-(2,3-Dichloro-phenoxymethyl)-[1,3,4]oxadiazol-2-yl]-heptyl}-N-hydroxy formamide;
N-Hydroxy-N-{(R)-2-[5-(4-methoxy-phenoxymethyl)-[1,3,4]oxadiazol-2-yl]-heptyl}-formamide;
N-((R)-2-{5-[4-(4-Acetyl-piperazin-1-yl)-phenoxymethyl]-[1,3,4]oxadiazol-2-yl}-heptyl)-N-hydroxy-formamide;
N-Hydroxy-N-{(R)-2-[5-(1-methyl-1H-pyrrol-2-ylmethyl)-[1,3,4]oxadiazol-2-yl]-heptyl}-formamide;
N-Hydroxy-N-[(R)-2-(5-pyridin-2-ylmethyl-[1,3,4]oxadiazol-2-yl)-heptyl]-formamide;
N-Hydroxy-N-[(R)-2-(5-pyridin-4-ylmethyl-[1,3,4]oxadiazol-2-yl)-heptyl]-formamide;
N-Hydroxy-N-{(R)-2-[5-(2,6-dichloro-benzyl)-[1,3,4]oxadiazol-2-yl]-heptyl}formamide,
N-Hydroxy-N-{(R)-2-[5-(1H-indol-3-ylmethyl)-[1,3,4]oxadiazol-2-yl]-heptyl}-formamide;
N-{(R)-2-[(S)-5-(2,3-Dihydro-benzo[1,4]dioxin-2-yl)-[1,3,4]oxadiazol-2-yl]-heptyl}-N-hydroxy-formamide;
N-[(R)-2-(5-Benzofuran-4-ylmethyl-[1,3,4]oxadiazol-2-yl)-heptyl]-N-hydroxyformamide;
N-Hydroxy-N-[(R)-2-(5-pyrimidin-2-yl-[1,3,4]oxadiazol-2-yl)-heptyl]-formamide;
N-{(R)-2-[5-(2,3-Dihydro-benzo[d]isoxazol-3-ylmethyl)-[1,3,4]oxadiazol-2-yl]-heptyl}-N-hydroxy-formamide;
N-Hydroxy-N-[(R)-2-(5-phenoxymethyl-[1,3,4]oxadiazol-2-yl)-heptyl]-formamide;
N-Hydroxy-N-{(R)-2-[(S)-5-(1,2,3,4-tetrahydro-isoquinolin-3-yl)-[1,3,4]oxadiazol-2-yl]-heptyl}-formamide;
N-Hydroxy-N-{(R)-2-[5-(4-imidazol-1-yl-phenoxymethyl)-[1,3,4]oxadiazol-2-yl]-heptyl}-formamide;

N-Hydroxy-N-{(R)-2-[5-(quinolin-6-yloxymethyl)-[1,3,4] oxadiazol-2-yl]-heptyl}-formamide;

5-{(R)-1-[(Formyl-hydroxy-amino)-methyl]-hexyl}-[1,3,4] oxadiazole-2-carboxylic acid phenylamide;

N-Hydroxy-N-[(R)-2-(5-phenylaminomethyl-[1,3,4]oxadiazol-2-yl)-heptyl]-formamide;

N-{(R)-2-[5-(2-Chloro-benzyl)-[1,3,4]oxadiazol-2-yl]-heptyl}-N-Hydroxy-formamide;

N-[(R)-2-(5-Benzyl-[1,3,4]oxadiazol-2-yl)-3-cyclohexyl-propyl]-N-hydroxyformamide;

N-((R)-2-{5-[2-(1H-Benzoimidazol-2-yl)-ethyl]-[1,3,4] oxadiazol-2-yl}-heptyl)-N-Hydroxy-formamide;

N-Hydroxy-N-{(R)-2-[5-(4-pyrimidin-2-yl-piperazin-1-ylmethyl)-[1,3,4]oxadiazol-2-yl]-heptyl}-formamide;

N-Hydroxy-N-{(R)-2-[5-(3-methyl-isoxazol-5-ylmethyl)-[1,3,4]oxadiazol-2-yl]-heptyl}-formamide;

N-Hydroxy-N-{(R)-2-[5-(5-methyl-2-phenyl-oxazol-4-ylmethyl)-[1,3,4]oxadiazol-2-yl]-heptyl}-formamide;

N-Hydroxy-N-(2-{5-[(4-trifluoromethyl-pyrimidin-2-ylamino)-methyl]-[1,3,4]oxadiazol-2-yl}-heptyl)-formamide;

N-{(R)-2-[5-(1H-Benzoimidazol-2-ylmethyl)-[1,3,4]oxadiazol-2-yl]-heptyl}-N-hydroxy-formamide;

N-Hydroxy-N-[(R)-2-(5-morpholin-4-ylmethyl-[1,3,4]oxadiazol-2-yl)-heptyl]-formamide;

N-Hydroxy-N-((R)-2-{5-[(3-trifluoromethyl-phenylamino)-methyl]-[1,3,4]oxadiazol-2-yl}-heptyl)-formamide;

N-[(R)-2-(5-Benzyl-[1,3,4]oxadiazol-2-yl)-3-cyclopentyl-propyl]-N-hydroxyformamide;

N-Hydroxy-N-[(R)-2-(5-methyl-[1,3,4]oxadiazol-2-yl)-heptyl]-formamide; and

N-Hydroxy-N-((R)-2-{5-[2-(1H-indol-3-yl)-ethyl]-[1,3,4] oxadiazol-2-yl}-heptyl)-formamide.

The following synthetic schemes are merely illustrative of the methods by which the compounds of the invention may be prepared and are not intended to limit the scope of the invention as defined in the appended claims.

As shown in Scheme 4, ester (29) can be submitted to hydrazinolysis to afford hydrazide (30).

As shown in Scheme 5, coupling of the carboxylic acid (8) with hydrazide (30) provides acylated hydrazide (31). Cyclization using a dehydrating agent such as Burgess reagent under microwave irradiation at 140° C. provides oxadiazole (32). Alternatively, the cyclization can be accomplished using triphenylphosphine with carbon tetrachloride and a base such as triethyl amine. Hydrogenolysis to remove the benzyl group using a catalyst, such as 10% Pd/C, in an appropriate solvent, such as ethanol, gives compound (33). Using this methodology, the chiral acid (17) or (25) provides the final compound (36) or (39).

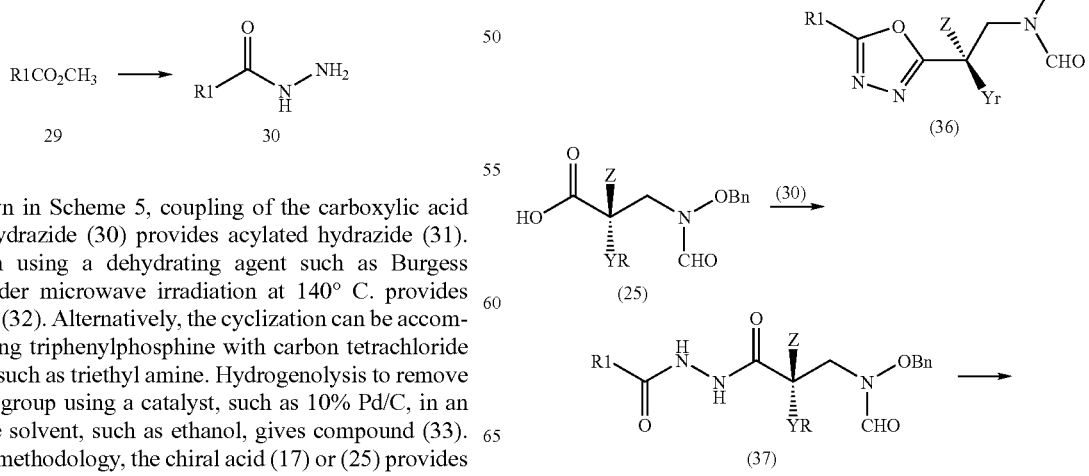

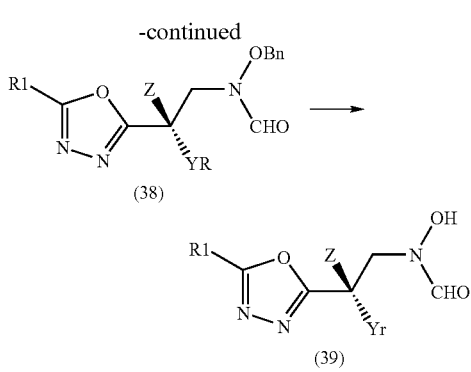

SYNTHETIC EXAMPLES

The invention will now be described by reference to the following examples which are merely illustrative and are not to be construed as a limitation of the scope of the present invention.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Hz (Hertz); TLC (thin layer chromatography);
$T_r$ (retention time); RP (reverse phase);
MeOH (methanol); i-PrOH (isopropanol);
EtOH (ethanol); TEA (triethylamine);
TFA (trifluoroacetic acid); THF (tetrahydrofuran);
DMSO (dimethylsulfoxide); AcOEt or EtOAc (ethyl acetate);
DCM (dichloromethane); DMF (N,N-dimethylformamide);
CDI (1,1-carbonyldiimidazole); HOAc (acetic acid);
HOSu (N-hydroxysuccinimide); Ac (acetyl);
HOBT (1-hydroxybenzotriazole); BOC (tert-butyloxycarbonyl);
mCPBA (meta-chloroperbenzoic acid); FMOC (9-fluorenylmethoxycarbonyl);
DCC (dicyclohexylcarbodiimide); CBZ (benzyloxycarbonyl);
NMM (N-methyl morpholine); HOAt (1-hydroxy-7-azabenzotriazole);
DMAP (4-dimethylaminopyridine); Bn (benzyl);
TBAF (tetra-n-butylammonium fluoride);
HPLC (high pressure liquid chromatography);
BOP (bis(2-oxo-3-oxazolidinyl)phosphinic chloride);
EDCI (1-ethyl-3-[3-dimethylaminopropyl]carbodiimide hydrochloride);
HBTU (O-Benzotriazole-1-yl-N,N,N',N'-tetramethyluronium hexafluorophosphate).

All references to ether are to diethyl ether, brine refers to a saturated aqueous solution of NaCl. Unless otherwise indicated, all temperatures are expressed in ° C. (degrees C.). All reactions are conducted under an inert atmosphere at room temperature unless otherwise noted, and all solvents are highest available purity unless otherwise indicated.

$^1$H NMR (hereinafter also "NMR") spectra were recorded on a Varian VXR-300, a Varian Unity-300, a Varian Unity-400 instrument, a Brucker AVANCE-400, a General Electric QE-300 or a Bruker AM 400 spectrometer. Chemical shifts are expressed in parts per million (ppm, δunits). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 4.5% to 90% $CH_3CN$ (0.02% TFA) in 3.2 min with a 0.4 min hold and 1.4 min re-equilibration; detection by MS, UV at 214 nm, and a light scattering detector (ELS). Column: 1×40 mm Aquasil (C18).

For preparative (prep) hplc; ca 50 mg of the final products were injected in 500 uL of DMSO onto a 50×20 mm 1. D. YMC CombiPrep ODS-A column at 20 mL/min with a 10 min gradient from 10% $CH_3CN$ (0.1% TFA) to 90% $CH_3CN$ (0.1% TFA) in $H_2O$ (0.1% TFA) and a 2 min hold. Flash chromatography was run over Merck Silica gel 60 (230–400 mesh).

Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution.

The compounds disclosed in Examples 2 to 42 were prepared following the general procedures described in Example 1.

Preparation 1

(4S)-Benzyl-3-heptanoyl-oxazolidin-2-one

To a solution of (S)-(−)-4-benzyl-2-oxazolidinone (3.3 g, 18.6 mmol) in THF (50 mL) at −78° C. was added dropwise n-BuLi (7.4 mL, 2.5M solution in hexane, 18.6 mmol). After stirring for 30 min at the same temperature, the reaction mixture was then treated with heptanoyl chloride (2.76 g, 18.6 mmol). The reaction mixture was stirred and allowed to warm to 10° C. over 5 h, and then quenched with saturated aqueous $NH_4Cl$ solution (100 mL). The aqueous layer was extracted with EtOAc (100 mL×2). The combined organic layers were washed with brine, and dried over $MgSO_4$. Removal of the solvent under reduced pressure yielded 4.63 g (86%) of the title compound. $^1$H NMR (400 MHz, $CDCl_3$) δ 7.37–7.22 (m, 5H), 4.69 (m, 1H), 4.19 (m, 2H), 3.31 (dd, J=13.4, 3.3 Hz, 1H), 2.95 (m, 2H), 2.79 (dd, J=13.4, 9.7 Hz, 1H), 1.71 (m, 2H), 1.42–1.32 (m, 6H), 0.92 (t, J=6.8 Hz, 3H). Mass spectrum ES+: 290 [M+H]$^+$.

Preparation 2

(4S)-Benzyl-3-[(2R)-benzyloxymethylheptanoyl]oxazolidin-2-one

To a solution of (S)-4-benzyl-3-heptanoyloxazolidin-2-one (4.63 g, 16.02 mmol) and titanium (IV) chloride (1.9 mL, 16.82 mmol) in dichloromethane (55 mL) at 0° C. was added dropwise diisopropylethylamine (3.1 mL, 17.62 mmol). After stirring at 0° C. for 1 hour, the resulting titanium enolate was then reacted with benzylchloromethyl ether (TCI-America, 4.9 mL, 32.04 mmol) at 0° C. for 6 h. The reaction mixture was then quenched with water (100 mL).

The aqueous layer was extracted with dichloromethane (100 mL×2). The organic extracts were washed with brine, and dried over MgSO4. After removing the solvent under reduced pressure, purification by flash column chromatography using an eluting system of hexane/EtOAc (5:1) yielded 4.39 g (67%) of the title compound. $^1$H NMR (400 MHz, CDCl$_3$) δ 7.38–7.21 (m, 10H), 4.74 (m, 1H), 4.57 (m, 2H), 4.28–4.13 (m, 3H), 3.82 (t, J=8.7 Hz, 1H), 3.68 (dd, J=9.0, 4.9 Hz, 1H), 3.25 (dd, J=13.5, 3.1 Hz, 1H), 2.71 (dd, J=13.5, 9.3 Hz, 1H), 1.74 (m, 1H), 1.54 (m, 1H), 1.31–1.28 (m, 6H), 0.89 (t, J=6.7 Hz, 3H). Mass spectrum ES+: 410 [M+H]$^+$.

Preparation 3

(3R)-Benzyloxy-2-pentylpropionic acid

A 0.05 M solution of (S)-4-benzyl-3-[(R)-2-benzyloxymethylheptanoyl]oxazolidin-2-one (2.0 g, 4.89 mmol) in a 3:1 mixture of THF and H$_2$O was treated with 30% H$_2$O$_2$ (4.5 mL, 39.12 mmol), followed by LiOH (0.48 g, 9.78 mmol) at 0° C. The resulting mixture was stirred and allowed to warm to room temperature overnight. THF was then removed under vacuum. The residue was washed with dichloromethane (50 mL×2) to remove (S)-4-benzyloxazolidin-2-one. The desired product was isolated by EtOAc extraction of the acidified (pH 1~2) aqueous phase. No further purification was required. Standing under high vacuum yielded 1.16 g (95%) of the title compound. $^1$H NMR (400 MHz, CHCl$_3$) δ 11.1 (br s, 1H), 7.36 (m, 5H), 4.57 (s, 2H), 3.69 (m, 1H), 3.58 (dd, J=9.2, 5.2 Hz, 1H), 2.74 (m, 1H), 1.66 (m, 1H), 1.54 (m, 1H), 1.34–1.30 (m, 6H), 0.90 (t, J=6.7 Hz, 3H). Mass spectrum ES+: 251 [M+H]$^+$.

Preparation 4

3-Hydroxy-(2R)-pentylpropionic acid

To a solution of (R)-3-benzyloxy-2-pentyl-propionic acid (1.54 g, 6.16 mmol) in EtOH (100 mL) was added 10% Pd/C (310 mg). The reaction mixture was subjected to hydrogenation overnight at room temperature. After the reaction was completed, the reaction mixture was filtered through a pad of Celite, and washed with EtOH (50 mL×3). Removal of the solvent provided the title compound (0.92 g, 93%). No further purification was required. $^1$H NMR (400 MHz, CHCl$_3$) δ 6.30 (br s, 1H), 3.81 (d, J=5.4 Hz, 2H), 2.64 (m, 1H), 1.69 (m, 1H), 1.56 (m, 1H), 1.41–1.27 (m, 6H), 0.91 (t, J=7.7 Hz, 3H). Mass spectrum ES+: 161 [M+H]$^+$.

Preparation 5

N-Benzyloxy-3-hydroxy-(2R)-pentylpropionamide

To a mixture of (R)-3-hydroxy-2-pentylpropionic acid (0.92 g, 5.75 mmol), O-benzyl hydroxylamine hydrochloride (0.92 g, 5.75 mmol) and 4-(dimethylamino)pyridine (1.41 g, 11.50 mmol) in dichloromethane (25 mL) at 0° C. was added 1-[3-(dimethylamino)propyl]-3-ethylcarbodiimide hydrochloride (1.11 g, 5.75 mmol). After stirring at room temperature overnight, the reaction was then quenched with 1N aqueous HCl solution (25 mL) and extracted using dichloromethane (25 mL×2). The organic extracts were washed with water, brine, and dried over MgSO$_4$. Removal of the solvent under reduced pressure yielded the title compound (1.43 g, 94%). $^1$H NMR (400 MHz, CHCl$_3$) δ 9.22 (br s, 1H), 7.41–7.28 (m, 5H), 4.89 (q, J=10.6 Hz, 2H), 3.70–3.37 (m, 3H), 2.17 (m, 1H), 1.54 (br s, 1H), 1.27 (m, 6H), 0.88 (t, J=6.9 Hz, 3H). Mass spectrum ES+: 266 [M+H]$^+$.

Preparation 6

1-benzyloxy-(3R)-pentylazetidin-2-one

To a mixture of (R)-N-benzyloxy-3-hydroxy-2-pentylpropionamide (1.41 g, 5.32 mmol) and triphenylphosphine (1.68 g, 6.39 mmol) in THF (53 mL) was added dropwise diethyl azodicarboxylate (1.1 mL, 6.39 mmol) at 0° C. The reaction mixture was stirred and allowed to warm to room temperature overnight. The reaction was then quenched with water (50 mL). The aqueous layer was extracted with EtOAc (50 mL×2). The combined organic layers were washed with brine, and dried over MgSO$_4$. After removing the solvent under vacuum, the residue was purified by flash column chromatography (hex:EtOAc 5/1) to provide the title compound (1.17 g, 89%). $^1$H NMR (400 MHz, CHCl$_3$) δ7.35–7.25 (m, 5H), 4.87 (s, 2H), 3.28 (t, J=4.85 Hx, 1H), 2.84 (q, J=2.35 Hz, 1H), 2.77 (m, 1H), 1.62 (m, 1H), 1.36 (m, 1H), 1.25–1.16 (m, 6H), 0.88 (t, J=6.9 Hz, 3H). Mass spectrum ES+: 248 [M+H]$^+$.

Preparation 7

3-benzyloxyamino-(2R)-pentylpropionic acid

To a mixture of (R)-1-benzyloxy-3-pentylazetidin-2-one (0.96 g, 3.89 mmol) in a mixture of THF—H$_2$O-MeOH (50 mL, 3:1:1 v/v) was added lithium hydroxide monohydrate (1.91 g, 38.9 mmol). After stirring at room temperature overnight, water (25 mL) was added to the mixture. The solution was acidified to pH 5~6 with 3N aqueous HCl solution. It was extracted with EtOAc (50 mL×2). The combined organic layers were dried over MgSO$_4$. Removal of the solvent under vacuum provided the title compound (0.98 g, 95%). $^1$H NMR (400 MHz, CHCl$_3$) δ 9.80 (br s, 1H), 7.37 (m, 5H), 4.75 (m, 2H), 3.14 (m, 2H), 2.74 (m, 1H), 1.70 (m, 1H), 1.53 (m, 1H), 1.38–1.25 (m, 6H), 0.91 (t, J=6.8 Hz, 3H). Mass spectrum ES+: 266 [M+H]$^+$.

Preparation 8

(2R)-[(benzyloxyformylamino)methyl]heptanoic acid

To a cold solution of (R)-3-Benzyloxyamino-2-pentylpropionic acid (1.03 g, 3.89 mmol) in HCO$_2$H (19 mL) and dichloromethane (19 mL) at 0° C. was added acetic anhydride (3.9 mL, 41.2 mmol). The mixture was stirred at 0° C. for 3 hours. The volatiles were removed by evaporation under vacuum. Dichloromethane (50 mL) was added to it. It was washed with brine (50 mL×2), and dried over MgSO$_4$. Filtration and evaporation under vacuum provided the title compound (1.08 g, 95%). $^1$H NMR (400 MHz, CHCl$_3$) δ 8.07 (br s, 1H), 7.29 (m, 5H), 4.91–4.71 (m, 2H), 3.76 (m, 2H), 2.67 (m, 1H), 1.54 (m, 1H), 1.41 (m, 1H), 1.20 (m, 6H), 0.80 (t, J=7.0 Hz, 3H). Mass spectrum ES+: 294 [M+H]$^+$.

Preparation 9

N-Benzylcarbonyl-N'-{(2R)-[(benzyloxyformylamino)methyl]heptanoyl}-hydrazine A mixture consisting of (2R)-[(benzyloxyformylamino)methyl]heptanoic acid (200 mg, 0.68 mmol), phenylacetic acid hydrazide (103 mg, 0.68 mmol), DMAP (100 mg, 0.82 mmol) and EDCI (158 mg, 0.82 mmol) in methylene chloride (3 ml) was stirred at room temperature for 18 h. The mixture was diluted with methylene chloride (10 ml) then washed with 1N HCl, water then brine. The organic extract was dried then removal of all volatiles in vacuo followed by purification by preparative HPLC provided the title compound (131 mg, 45%). Mass spectrum ES+: 426 [M+H]+.

Preparation 10

N-[(R)-2-(5-Benzyl-[1,3,4]oxadiazol-2-yl)-heptyl]-N-benzyloxy formamide

A solution of N-benzylcarbonyl-N'-{(2R)-[(benzyloxyformylamino) methyl]heptanoyl}-hydrazine (105 mg, 0.25 mmol) with Burgess reagent (147 mg, 0.62 mmol) in THF (3 ml) was subjected to microwave irradiation at 140° C. for 10 min. The mixture was diluted with EtOAc (15 ml) then washed with water then brine, dried and solvent removed to provide the title compound as a yellow oil (108 mg). Mass spectrum ES+: 408 [M+H]+

Example 1

N-[(R)-2-(5-Benzyl-[1,3,4]oxadiazol-2-yl)-heptyl]-N-hydroxyformamide

A mixture consisting of N-[(R)-2-(5-benzyl-[1,3,4]oxadiazol-2-yl)-heptyl]-N-benzyloxy formamide (108 mg crude) with 10% palladium on carbon was stirred under an atmosphere of hydrogen for 5.5 h. The mixture was filtered and solvent removed in vacuo. Purification by preparative HPLC provided the title compound (30 mg, 38% for two steps). Mass spectrum ES+: 318 [M+H]+

Preparation 11

Benzol[1,3]dioxole-5-carboxylic acid hydrazide

A solution of methyl benzo[1,3]dioxole-5-carboxylate (1.80 g, 10 mmol) in methanol (50 ml) with hydrazene hydrate (0.97 ml) was stirred at room temperature for 20 h. Removal of all volatiles in vacuo provided the title compound (1.73 g, 96%) MH+ 181.

Example 2

N-[(R)-2-(5-Benzo[1,3]dioxol-5-yl-[1,3,4]oxadiazol-2-yl)-heptyl]-N-hydroxyformamide Purification by preparative HPLC yielded 9 mg of the title compound. MH+ 348

Example 3

N-hydroxy-N-{(R)-2-[5-(7-methoxy-benzofuran-2-yl)[1,3,4]oxadiazol-2-yl]-heptyl}-formamide Purification by preparative HPLC yielded 44 mg (27% two steps) of the title compound. Mass spectrum ES+: 374 [M+H]+

Example 4

N-hydroxy-N-{(R)-2-[5-(1,2,3,4-tetrahydroquinolin-6-yl)-[1,3,4]oxadiazol-2-yl]-heptyl}-formamide Purification by preparative HPLC yielded 16.3 mg (39% two steps) of the title compound. Mass spectrum ES+: 359 [M+H]+

Example 5

N-hydroxy-N-{(R)-2-[5-(1,2,3,4-tetrahydro-quinolin-8-yl)-[1,3,4]oxadiazol-2-yl]-heptyl}-formamide Purification by preparative HPLC yielded 17 mg (40% two steps) of the title compound. Mass spectrum ES+: 359 [M+H]+

Example 6

N-hydroxy-N-[(R)-2-(5-pyridin-3-ylmethyl-[1,3,4]oxadiazol-2-yl)-heptyl]-formamide Purification by preparative HPLC yielded 35 mg (41% two steps) of the title compound. Mass spectrum ES+: 319 [M+H]+

Example 7

N-{(R)-2-[5-(3,4-Dichloro-benzyl)-[1,3,4]oxadiazol-2-yl]-heptyl}-N-hydroxyformamide Purification by preparative HPLC yielded 10 mg (14% two steps) of the title compound. Mass spectrum ES+: 386 [M+H]+

Example 8

N-{(R)-2-[5-(3,4-dimethoxy-benzyl)-[1,3,4]oxadiazol-2-yl]-heptyl}-N-hydroxyformamide Purification by preparative HPLC yielded 39 mg (35% two steps) of the title compound. Mass spectrum ES+: 378 [M+H]+

Example 9

N-[(R)-2-(5-Benzo[1,3]dioxol-5-ylmethyl-[1,3,4]oxadiazol-2-yl)-heptyl]-N-hydroxy-f ormamide Purification by preparative HPLC yielded 33 mg (37% two steps) of the title compound. Mass spectrum ES+: 362 [M+H]+

Example 10

N-hydroxy-N-{(R)-2-[5-(2-morpholin-4-yl-ethyl)-[1,3,4]oxadiazol-2-yl]-heptyl}-formamide Purification by preparative HPLC yielded 51 mg (50% two steps) of the title compound. Mass spectrum ES+: 341 [M+H]+

Example 11

N-hydroxy-{(R)-2-[5-(6-methoxy-benzofuran-2-ylmethyl)[1,3,4]oxadiazol-2-yl]-heptyl}-formamide Purification by preparative HPLC yielded 19 mg (18% two steps) of the title compound. Mass spectrum ES+: 388 [M+H]+

Example 12

N-{(R)-2-[5-(2,3-Dichloro-phenoxymethyl)-[1,3,4]oxadiazol-2-yl]-heptyl}-N-hydroxy formamide Purification by preparative HPLC yielded 30 mg (28% two steps) of the title compound. Mass spectrum ES+: 402 [M+H]+

Example 13

N-hydroxy-N-{(R)-2-[5-(4-methoxy-phenoxymethyl)-[1,3,4]oxadiazol-2-yl]-heptyl}-formamide Purification by preparative HPLC yielded 30 mg (42% two steps) of the title compound. Mass spectrum ES+: 364 [M+H]+

Example 14

N-((R)-2-{5-[4-(4-Acetyl-piperazin-1-yl)-phenoxymethyl]-[1,3,4]oxadiazol-2-yl}-heptyl)-N-hydroxy-formamide Purification by preparative HPLC yielded 20 mg (20% two steps) of the title compound. Mass spectrum ES+: 460 [M+H]+

Example 15

N-hydroxy-N-{(R)-2-[5-(1-methyl-1H-pyrrol-2-ylmethyl)-[1,3,4]oxadiazol-2-yl]-heptyl}-formamide Purification by preparative HPLC yielded 20 mg (21% two steps) of the title compound. Mass spectrum ES+: 321 [M+H]+

Example 16

N-hydroxy-N-[(R)-2-(5-pyridin-2-ylmethyl-[1,3,4]oxadiazol-2-yl)-heptyl]-formamide Purification by preparative HPLC yielded 73 mg (58% two steps) of the title compound. Mass spectrum ES+: 419 [M+H]+

Example 17

N-hydroxy-N-[(R)-2-(5-pyridin-4-ylmethyl-[1,3,4]oxadiazol-2-yl)-heptyl]-formamide Purification by preparative HPLC yielded 25 mg (21% two steps) of the title compound. Mass spectrum ES+: 419 [M+H]+

Example 18

N-hydroxy-N-{(R)-2-[5-(2,6-dichloro-benzyl)-[1,3,4]oxadiazol-2-yl]-heptyl}formamide Purification by preparative HPLC yielded 20 mg (16% two steps) of the title compound. Mass spectrum ES+: 419 [M+H]+

Example 19

N-Hydroxy-N-{(R)-2-[5-(1H-indol-3-ylmethyl)-[1,3,4]oxadiazol-2-yl]-heptyl}-formamide Purification by preparative HPLC yielded 20 mg (45% two steps) of the title compound. Mass spectrum ES+: 357 [M+H]+

Example 20

N-{(R)-2-[(S)-5-(2,3-Dihydro-benzo[1,4]dioxin-2-yl)-[1,3,4]oxadiazol-2-yl]-heptyl}-N-hydroxy-formamide Purification by preparative HPLC yielded 37 mg (41% two steps) of the title compound. Mass spectrum ES+: 362 [M+H]+

Example 21

N-[(R)-2-(5-Benzofuran-4-ylmethyl-[1,3,4]oxadiazol-2-yl)-heptyl]-N-hydroxy-formamide Purification by preparative HPLC yielded 40 mg (37% two steps) of the title compound. Mass spectrum ES+: 358 [M+H]+

Example 22

N-hydroxy-N-[(R)-2-(5-pyrimidin-2-yl-[1,3,4]oxadiazol-2-yl)-heptyl]-formamide

Purification by preparative HPLC yielded 18 mg (18% two steps) of the title compound. Mass spectrum ES+: 306 [M+H]+

Example 23

N-{(R)-2-[5-(2,3-Dihydro-benzo[d]isoxazol-3-ylmethyl)-[1,3,4]oxadiazol-2-yl]-heptyl}-N-hydroxy-formamide Purification by preparative HPLC yielded 10 mg (13% two steps) of the title compound. Mass spectrum ES+: 361 [M+H]+

Example 24

N-hydroxy-N-[(R)-2-(5-phenoxymethyl-[1,3,4]oxadiazol-2-yl)-heptyl]-formamide

Purification by preparative HPLC yielded 25 mg (30% two steps) of the title compound. Mass spectrum ES+: 334 [M+H]$^+$

Example 25

N-hydroxy-N-{(R)-2-[(S)-5-(1,2,3,4-tetrahydro-isoquinolin-3-yl)-[1,3,4]oxadiazol-2-yl]-heptyl}-formamide Purification by preparative HPLC yielded 24 mg (35% two steps) of the title compound. Mass spectrum ES+: 359 [M+H]$^+$

Example 26

N-hydroxy-N-{(R)-2-[5-(4-imidazol-1-yl-phenoxymethyl)-[1,3,4]oxadiazol-2-yl-heptyl}-formamide Purification by preparative HPLC yielded 47 mg (31% two steps) of the title compound. Mass spectrum ES+: 400 [M+H]$^+$

Example 27

N-hydroxy-N-{(R)-2-[5-(quinolin-6-yloxymethyl)-[1,3,4]oxadiazol-2-yl]-heptyl}-formamide Purification by preparative HPLC yielded 62 mg (32% two steps) of the title compound. Mass spectrum ES+: 385 [M+H]$^+$

Example 28

5-{(R)-1-[(Formyl-hydroxy-amino)-methyl]-hexyl}-[1,3,4]oxadiazole-2-carboxylic acid phenylamide Purification by preparative HPLC yielded 41 mg (34% two steps) of the title compound. Mass spectrum ES+: 347 [M+H]$^+$

Example 29

N-Hydroxy-N-[(R)-2-(5-phenylaminomethyl-[1,3,4]oxadiazol-2-yl)-heptyl]-formamide Purification by preparative HPLC yielded 37 mg (22% two steps) of the title compound. Mass spectrum ES+: 333 [M+H]$^+$

Example 30

N-{(R)-2-[5-(2-chloro-benzyl)-[1,3,4]oxadiazol-2-yl]-heptyl}-N-Hydroxyformamide

Purification by preparative HPLC yielded 10 mg of the title compound. Mass spectrum ES+: 352 [M+H]$^+$

Example 31

N-[(R)-2-(5-Benzyl-[1,3,4]oxadiazol-2-yl)-3-cyclohexyl-propyl]-N-hydroxyformamide Purification by preparative HPLC yielded 20 mg (34% two steps) of the title compound. Mass spectrum ES+: 344 [M+H]$^+$

Example 32

N-((R)-2-{5-[2-(1H-Benzoimidazol-2-yl)-ethyl]-[1,3,4]oxadiazol-2-yl}-heptyl)-N-Hydroxy-formamide Purification by preparative HPLC yielded 72 mg (52% two steps) of the title compound. Mass spectrum ES+: 372 [M+H]$^+$

Example 33

N-Hydroxy-N-{(R)-2-[5-(4-pyrimidin-2-yl-piperazin-1-ylmethyl)-[1,3,4]oxadiazol-2-yl]-heptyl}-formamide Purification by preparative HPLC yielded 26 mg of the title compound. Mass spectrum ES+: 404 [M+H]$^+$

Example 34

N-hydroxy-N-{(R)-2-[5-(3-methyl-isoxazol-5-ylmethyl)-[1,3,4]oxadiazol-2-yl]-heptyl}-formamide Purification by preparative HPLC yielded 7 mg of the title compound. Mass spectrum ES+: 373 [M+H]$^+$

Example 35

N-hydroxy-N-{(R)-2-[5-(5-methyl-2-phenyl-oxazol-4-ylmethyl)-[1,3,4]oxadiazol-2-yl]-heptyl}-formamide Purification by preparative HPLC yielded 96 mg (64% two steps) of the title compound. Mass spectrum ES+: 399 [M+H]$^+$

Example 36

N-Hydroxy-N-(2-{5-[(4-trifluoromethyl-pyrimidin-2-ylamino)-methyl]-[1,3,4]oxadiazol-2-yl}-heptyl)-formamide Purification by preparative HPLC yielded 25 mg (29% two steps) of the title compound. Mass spectrum ES+: 403 [M+H]$^+$

Example 37

N-{(R)-2-[5-(1H-Benzoimidazol-2-ylmethyl)-[1,3,4]oxadiazol-2-yl]-heptyl}-N-hydroxy-formamide Purification by preparative HPLC yielded 18 mg (28% two steps) of the title compound. Mass spectrum ES+: 358 [M+H]$^+$

Example 38

N-hydroxy-N-[(R)-2-(5-morpholin-4-ylmethyl-[1,3,4]oxadiazol-2-yl)-heptyl]-formamide Purification by preparative HPLC yielded 65 mg (46% two steps) of the title compound. Mass spectrum ES+: 327 [M+H]$^+$

Example 39

N-hydroxy-N-((R)-2-{5-[(3-trifluoromethyl-phenylamino)-methyl]-[1,3,4]oxadiazol-2-yl}-heptyl)-formamide Purification by preparative HPLC yielded 54 mg (66% two steps) of the title compound. Mass spectrum ES+: 401 [M+H]$^+$

Example 40

N-[(R)-2-(5-Benzyl-[1,3,4]oxadiazol-2-yl)-3-cyclopentyl-propyl]-N-hydroxyformamide Purification by preparative HPLC yielded 43 mg (59% two steps) of the title compound. Mass spectrum ES+: 330 [M+H]$^+$

Example 41

N-hydroxy-N-[(R)-2-(5-methyl-[1,3,4]oxadiazol-2-yl)-heptyl]-formamide

Purification by preparative HPLC yielded 24 mg (27% two steps) of the title compound. Mass spectrum ES+: 242 [M+H]$^+$

Example 42

N-hydroxy-N-((R)-2-{5-[2-(1H-indol-3-yl)-ethyl]-[1,3,4]oxadiazol-2-yl}-heptyl)-formamide Purification by preparative HPLC yielded 86 mg (58% two steps) of the title compound. Mass spectrum ES+: 371 [M+H]$^+$

Third Embodiment

As the third embodiment of the present invention, the compounds of Formula (1) with X=NR2 are disclosed, as in the racemic compound (40) and the chiral compounds (41) and (42). These compounds have preferentially R1=H and Z=H.

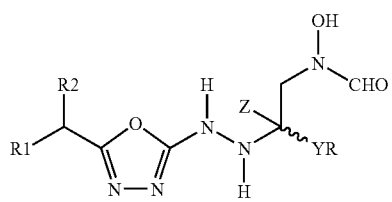
(40)

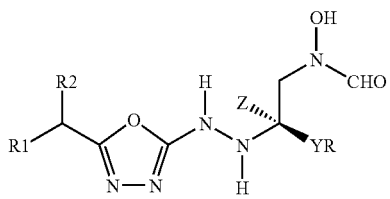
(41)

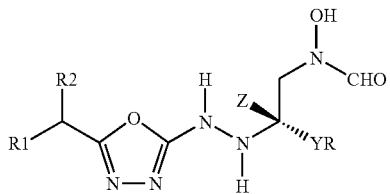
(42)

Preferred compounds useful in the present invention are selected from the group consisting of:
N-Hydroxy-[(R)-2-(5-phenylamino-[1,3,4]oxadiazol-2-yl)-heptyl]-formamide;
N-(5-{(R)-1-[(Formyl-hydroxy-amino)-methyl]-hexyl}-[1,3,4]oxadiazol-2-yl]benzamide;
N-{(R)-2-[5-(Chloro-trifluoromethyl-phenylamino)-[1,3,4]oxadiazol-2-yl]-heptyl}-N-hydroxy-formamide;
N-Hydroxy-N-{(R)-2-[5-(methyl-phenyl-amino)-[1,3,4]oxadiazol-2-yl]-heptyl}-formamide;
Benzo[1,3]dioxole-5-carboxylic acid(5-{(R)-1-[(formyl-hydroxy-amino)methyl]-hexyl}-[1,3,4]oxadiazol-1,2-yl)-amide;
N-{(R)-2-[5-(3,5-Dichloro-phenylamino)-[1,3,4]oxadiazol-2-yl]-heptyl}-N-hydroxy formamide;
N-[(S)-2-Fluoro-2-(5-phenylamino-[1,3,4]oxadiazol-2-yl)-heptyl]-N-hydroxy formamide; and
N-{(R)-2-[5-(2,3-Dihydro-benzo[1,4]dioxin-6-ylamino)-[1,3,4]oxadiazol-2-yl]-heptyl}-N-hydroxy-formamide.

The following synthetic schemes are merely illustrative of the methods by which the compounds of the invention may be prepared and are not intended to limit the scope of the invention as defined in the appended claims.

As shown in Scheme 6, treatment of the carbamyl chloride R1R2NC(O)Cl (43) with hydrazine affords semicarbazide (44). Alternatively, reacting the isocyanate R2NCO (45) with hydrazine affords the semicarbazide (44) wherein R2=H.

Scheme 6.

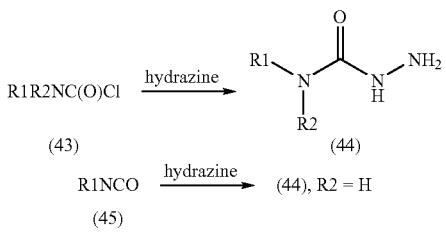

As shown in Scheme 7, coupling of the carboxylic acid (8) with semicarbazide (44) provides acylated semicarbazide (46). Cyclization using a dehydrating agent such as Burgess reagent under microwave irradiation at 140° C. provides the oxadiazole. Alternatively, the cyclization can be accomplished using triphenylphosphine with carbontetrachloride and a base such as triethyl amine in a suitable solvent such as acetonitrile. Hydrogenolysis to remove the benzyl group using a catalyst, such as 10% Pd/C, in an appropriate solvent, such as ethanol, gives compound (47). Using this methodology, the chiral acid (17) or (25) provide the final compound (49) or (51).

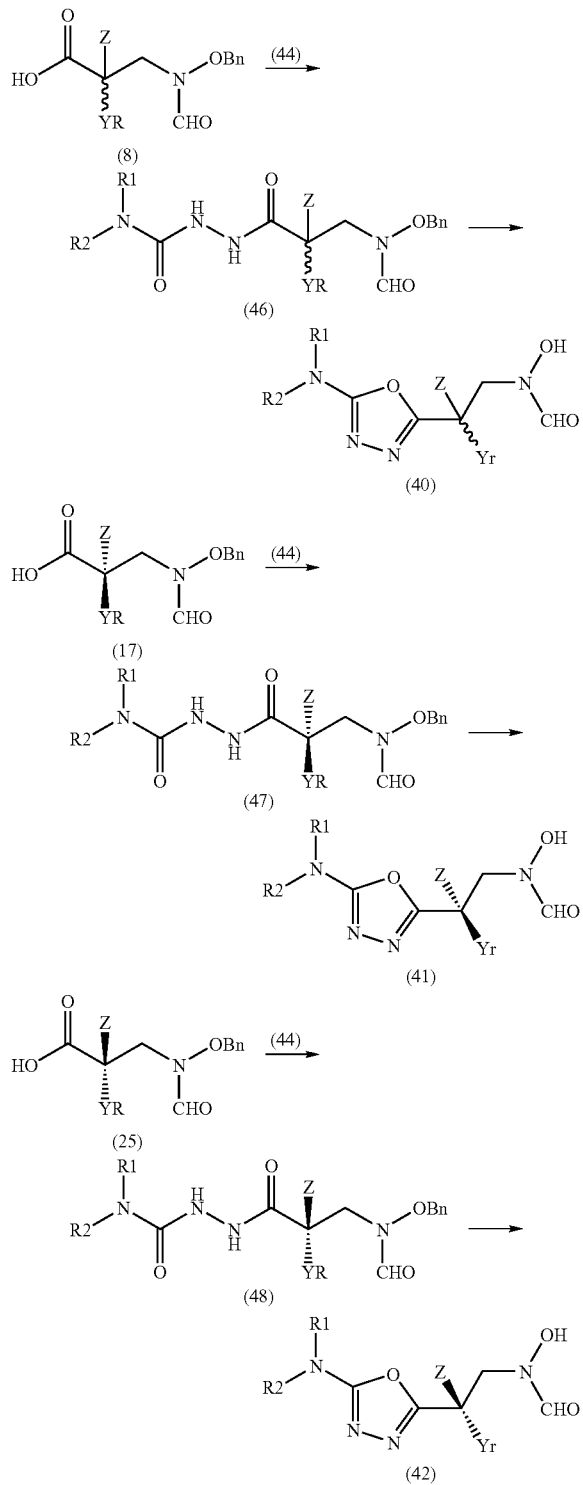

Scheme 7.

SYNTHETIC EXAMPLES

The invention will now be described by reference to the following examples which are merely illustrative and are not to be construed as a limitation of the scope of the present invention. The same experimental general conditions and conventions described in the Experimental Section of the Second Embodiment are applicable here.

The compounds disclosed in Examples 31 to 51 were prepared following the general procedures described in Example 1.

Preparation 12

4-(4-chloro-3-trifluoromethylhenyl)semicarbazide

To a solution of 4-chloro-3-trifluoromethylphenylisocyanate (806 mg, 3.61 mmol) in benzene (36 mL) at room temperature was added hydrazine hydrate (0.177 ml, 3.64 mmol). The reaction mixture was 1.5 h at room temperature. Evaporation under vacuum, followed by purification by preparative HPLC provided the title compound as a white powder (576 mg, 62%). MH+ 254.

Example 43

N-{(R)-2-[5-(Chloro-trifluoromethyl-phenylamino)-[1,3,4]oxadiazol-2-yl]-heptyl}-N-hydroxy-formamide Purification by preparative HPLC yielded 20 mg (15% two steps) of the title compound. Mass spectrum ES+: 421 [M+H]$^+$

Example 44

N-(5-{(R)-1-[(Formyl-hydroxy-amino)-methyl]-hexyl}-[1,3,4]oxadiazol-2-yl)-benzamide Purification by preparative HPLC yielded 25 mg (12% two steps) of the title compound. Mass spectrum ES+: 347 [M+H]$^+$

Example 45

N-hydroxy-[(R)-2-(5-phenylamino-[1,3,4]oxadiazol-2-yl)-heptyl]-formamide

Purification by preparative HPLC yielded 35 mg (17% two steps) of the title compound. Mass spectrum ES+: 319 [M+H]$^+$

Example 46

N-hydroxy-N-{(R)-2-[5-(N-methyl-N-phenylamino)-[1,3,4]oxadiazol-2-yl]-heptyl}-formamide Purification by preparative HPLC yielded 60 mg (54% two steps) of the title compound. Mass spectrum ES+: 333 [M+H]$^+$

Example 47

Benzo[1,3]dioxole-5-carboxylic acid(5-{(R)-1-[(formyl-hydroxy-amino)-methyl]-hexyl}-[1,3,4]oxadiazol-1,2-yl)-amide Purification by preparative HPLC yielded 27 mg (15% two steps) of the title compound. Mass spectrum ES+: 391 [M+H]$^+$

Example 48

N-{(R)-2-[5-(3,5-Dichloro-phenylamino)-[1,3,4]oxadiazol-2-yl]-heptyl}-N-hydroxy-formamide Purification by preparative HPLC yielded 8.5 mg (8%+24% monochloro compound) of the title compound. Mass spectrum ES+: 387 [M+H]$^+$

Preparation 13

(4S)-Benzyl-3-(2-fluoroheptanoyl)oxazolidin-2-one

To a solution of (4S)-benzyl-3-heptanoyl-oxazolidin-2-one (12.0 g, 41.4 mmol) in THF (30 ml) stirred under $N_2$ at −78° C. was added dropwise a solution of lithium bis(trimethylsilyl)amide (50 ml of 1 M soln. in THF, 50 mmol). This was stirred 1 h at −78° C. then added to solution of N-fluorobenzenesulfonamide (14.3 g, 45.5 mmol) in THF (60 ml) stirred under $N_2$ at −78° C. The reaction mixture was stirred 2.5 h at −78° C. then quenched with aqueous amonium chloride. The product mixture was partitioned between EtOAc and water. The organic extract was washed with brine, dried and all volitiles removed. Chromatography on silica (10% EtOAc 90% hexane) afforded 10.08 g (79%) of the title compound. Mass spectrum ES+: 308 [M+H]$^+$

Example 49

N-[(S)-2-Fluoro-2-(5-phenylamino-[1,3,4]oxadiazol-2-yl)-heptyl]-N-hydroxy formamide Purification by preparative HPLC yielded 70 mg (50% three steps) of the title compound. Mass spectrum ES+: 337 [M+H]$^+$

Example 50

N-{(R)-2-[5-(2,3-Dihydrobenzo[1,4]dioxin-6-ylamino)-[1,3,4]oxadiazol-2-yl]-heptyl}-N-hydroxy-formamide Purification by preparative HPLC yielded 46 mg (27% two steps) of the title compound. Mass spectrum ES+: 377 [M+H]$^+$

COMPOSITIONS, ADMINISTRATION AND BIOLOGICAL ASSAYS

Compounds of Formula (1) and their pharmaceutically acceptable salts may be administered in a standard manner for antibiotics, for example orally, parenterally, sub-lingually, dermally, transdermally, rectally, via inhalation or via buccal administration.

Compositions of Formula (1) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils, and incorporated in a soft gelatin capsule shell.

Typical parenteral compositions consist of a solution or suspension of a compound or salt in a sterile aqueous or non-aqueous carrier optionally containing a parenterally acceptable oil, for example, polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example, polymeric glycols, gelatins, cocoa-butter or other low melting vegetable waxes or fats or their synthetic analogs.

Typical dermal and transdermal formulations comprise a conventional aqueous or non-aqueous vehicle, for example, a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (1).

The daily dosage regimen for oral administration is suitably about 0.01 mg/Kg to 40 mg/Kg of a compound of Formula (1) or a pharmaceutically acceptable salt thereof calculated as the free acid. The daily dosage regimen for parenteral administration is suitably about 0.001 mg/Kg to 40 mg/Kg of a compound of Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (1) are demonstrated by the following test:

Biological Assay

S. aureus or E. coli PDF activity is measured at 25° C., using a continuous enzyme-linked assay developed by Lazennec & Meinnel ("Formate dehydrogenase-coupled spectrophotometric assay of peptide deformylase", Anal. Biochem 1997, 244, pp. 180–182), with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Staphylococcus aureus* WCUH29, *Enterococcus faecalis* I, *Enterococcus faecalis* 7, *Haemophilus influenzae* Q1, *Haemophilus influenzae* NEMC1, *Moraxella catarrhalis* 1502, *Streptococcus pneumoniae* 1629, *Streptococcus pneumoniae* N1387, *Streptococcus pneumoniae* N1387, *E. coli* 7623 (AcrABEFD+) and *E. coli* 120 (AcrAB−). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (I):

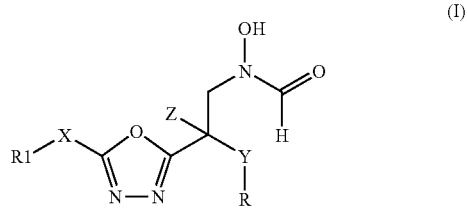

wherein:
X is selected from the group consisting of: $(CH_2)_n$, NR2, O, NR2CO, CONR2 and a bond;
Y is selected from the group consisting of: O, $CH_2$ and a covalent bond;
Z is selected from the group consisting of: hydrogen and fluorine;
R is selected from the group consisting of:
$C_{2-6}$ alkyl optionally substituted by alkoxy, halogen, or $C_{1-3}$ alkylsulfanyl; $C_{2-6}$ alkenyl optionally substituted by alkoxy, halogen, or $C_{1-3}$ alkylsulfanyl; $C_{2-6}$ alkynyl optionally substituted by alkoxy, halogen, or $C_{1-3}$ alkylsulfanyl; $(CH_2)_n$—$C_{3-6}$ carbocycle optionally substituted by alkoxy, halogen, or $C_{1-3}$ alkylsulfanyl; and $(CH_2)_n$—R3;
R1 is selected from the group consisting of:
hydrogen, $C_{1-3}$ substituted alkyl, $C_{2-3}$ substituted alkenyl, $C_{2-3}$ substituted alkynyl, $(CH_2)_n$—$C_{3-6}$ substituted carbocycle, aryl, heteroaryl, heterocyclic, and aminocarbonyl; provided that X is $(CH_2)_n$ when $R_1$ represents aminocarbonyl;
R2 is selected from the group consisting of:
hydrogen and $C_{1-3}$ substituted alkyl;
R3 is selected from the group consisting of:
phenyl, furan, benzofuran, thiophene, benzothiophene, tetrahydrofuran, tetrahydropyran, dioxane, 1,4-benzodioxane and benzo[1,3]dioxole, each of which is optionally substituted by one or more substituents each independently selected from: Cl, Br, I, $C_{1-3}$ alkyl optionally substituted by one to three F, and $C_{1-2}$ alkoxy, optionally substituted by one to three F; and
n represents an integer between 0 and 2; or a pharmaceutically acceptable salt or solvate thereof.

2. A compound according to claim 1, or a pharmaceutically acceptable salt or solvate thereof, with the following absolute configuration:

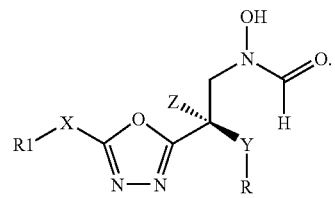

3. A compound according to claim 1, wherein X is $CH_2$ or a bond; or a pharmaceutically acceptable salt or solvate thereof.

4. A compound according to claim 1, wherein X is NR2; or a pharmaceutically acceptable salt or solvate thereof.

5. A compound according to claim 3 selected from the group consisting of:

N-[(R)-2-(5-Benzo[1,3]dioxol-5-yl-[1,3,4]oxadiazol-2-yl)-heptyl]-N-hydroxyformamide;

N-[(R)-2-(5-Benzyl-[1,3,4]oxadiazol-2-yl)-heptyl]-N-hydroxyformamide;

N-Hydroxy-N-{(R)-2-[5-(7-methoxy-benzofuran-2-yl)-[1,3,4]oxadiazol-2-yl]-heptyl}-formamide;

N-Hydroxy-N-{(R)-2-[5-(1,2,3,4-tetrahydroquinolin-6-yl)-[1,3,4]oxadiazol-2-yl]-heptyl}-formamide;

N-Hydroxy-N-{(R)-2-[5-(1,2,3,4-tetrahydro-quinolin-8-yl)-[1,3,4]oxadiazol-2-yl]-heptyl}-formamide;

N-Hydroxy-N-[(R)-2-(5-pyridin-3-ylmethyl-[1,3,4]oxadiazol-2-yl)-heptyl]-formamide;

N-{(R)-2-[5-(3,4-Dichloro-benzyl)-[1,3,4]oxadiazol-2-yl]-heptyl}-N-hydroxy-formamide;

N-{(R)-2-[5-(3,4-Dichloro-benzyl)-[1,3,4]oxadiazol-2-yl]-heptyl}-N-hydroxy-formamide;

N-{(R)-2-[5-(3,4-Dichloro-benzyl)-[1,3,4]oxadiazol-2-yl]-heptyl}-N-hydroxy-formamide;
N-Hydroxy-N-{(R)-2-[5-(2-morpholin-4-yl-ethyl)-[1,3,4]oxadiazol-2-yl]-heptyl}-formamide;
N-Hydroxy-N-{(R)-2-[5-(2-morpholin-4-yl-ethyl)-[1,3,4]oxadiazol-2-yl]-heptyl}-formamide;
N-{(R)-2-[5-(2,3-Dichloro-phenoxymethyl)-[1,3,4]oxadiazol-2-yl]-heptyl}-N-hydroxy formamide;
N-Hydroxy-N-{(R)-2-[5-(4-methoxy-phenoxymethyl)-[1,3,4]oxadiazol-2-yl]-heptyl}-formamide;
N-((R)-2-{5-[4-(4-Acetyl-piperazin-1-yl)-phenoxymethyl]-[1,3,4]oxadiazol-2-yl}-heptyl)-N-hydroxy-formamide;
N-Hydroxy-N-{(R)-2-[5-(1-methyl-1H-pyrrol-2-ylmethyl)-[1,3,4]oxadiazol-2-yl]-heptyl}-formamide;
N-Hydroxy-N-[(R)-2-(5-pyridin-2-ylmethyl-[1,3,4]oxadiazol-2-yl)-heptyl]formamide;
N-Hydroxy-N-[(R)-2-(5-pyridin-4-ylmethyl-[1,3,4]oxadiazol-2-yl)-heptyl]-formamide;
N-Hydroxy-N-{(R)-2-[5-(2,6-dichloro-benzyl)-[1,3,4]oxadiazol-2-yl]-heptyl}formamide;
N-Hydroxy-N-{(R)-2-[5-(1H-indol-3-ylmethyl)-[1,3,4]oxadiazol-2-yl]-heptyl}-formamide;
N-{(R)-2-[(S)-5-(2,3-Dihydro-benzo[1,4]dioxin-2-yl)-[1,3,4]oxadiazol-2-yl]-heptyl}-N-hydroxy-formamide;
N-[(R)-2-(5-Benzofuran-4-ylmethyl-[1,3,4]oxadiazol-2-yl)-heptyl]-N-hydroxy-formamide;
N-Hydroxy-N-[(R)-2-(5-pyrimidin-2-yl-[1,3,4]oxadiazol-2-yl)-heptyl]-formamide;
N-{(R)-2-[5-(2,3-Dihydro-benzo[d]isoxazol-3-ylmethyl)-[1,3,4]oxadiazol-2-yl]-heptyl}-N-hydroxy-formamide;
N-Hydroxy-N-[(R)-2-(5-phenoxymethyl-[1,3,4]oxadiazol-2-yl)-heptyl]-formamide;
N-Hydroxy-N-{(R)-2-[(S)-5-(1,2,3,4-tetrahydro-isoquinolin-3-yl)-[1,3,4]oxadiazol-2-yl]-heptyl}-formamide;
N-Hydroxy-N-{(R)-2-[5-(4-imidazol-1-yl-phenoxymethyl)-[1,3,4]oxadiazol-2-yl]-heptyl}-formamide;
N-Hydroxy-N-{(R)-2-[5-(quinolin-6-yloxymethyl)-[1,3,4]oxadiazol-2-yl]-heptyl}-formamide;
5-{(R)-1-[(Formyl-hydroxy-amino)-methyl]-hexyl}-[1,3,4]oxadiazole-2-carboxylic acid phenylamide;
N-Hydroxy-N-[(R)-2-(5-phenylaminomethyl-[1,3,4]oxadiazol-2-yl)-heptyl]-formamide;
N-{(R)-2-[5-(2-Chloro-benzyl)-[1,3,4]oxadiazol-2-yl]-heptyl}-N-Hydroxy-formamide;
N-[(R)-2-(5-Benzyl-[1,3,4]oxadiazol-2-yl)-3-cyclohexyl-propyl]-N-hydroxyformamide;
N-((R)-2-{5-[2-(1H-Benzoimidazol-2-yl)-ethyl]-[1,3,4]oxadiazol-2-yl}-heptyl)-N-Hydroxy-formamide;
N-Hydroxy-N-{(R)-2-[5-(4-pyrimidin-2-yl-piperazin-1-ylmethyl)-[1,3,4]oxadiazol-2-yl]-heptyl}-formamide;
N-Hydroxy-N-{(R)-2-[5-(3-methyl-isoxazol-5-ylmethyl)-[1,3,4]oxadiazol-2-yl]-heptyl}-formamide;
N-Hydroxy-N-{(R)-2-[5-(5-methyl-2-phenyl-oxazol-4-ylmethyl)-[1,3,4]oxadiazol-2-yl]-heptyl}-formamide;
N-Hydroxy-N-(2-{5-[(4-trifluoromethyl-pyrimidin-2-ylamino)-methyl]-[1,3,4]oxadiazol-2-yl}-heptyl)-formamide;
N-{(R)-2-[5-(1H-Benzoimidazol-2-ylmethyl)-[1,3,4]oxadiazol-2-yl]-heptyl}-N-hydroxy-formamide;
N-Hydroxy-N-[(R)-2-(5-morpholin-4-ylmethyl-[1,3,4]oxadiazol-2-yl)-heptyl]-formamide;
N-Hydroxy-N-((R)-2-{5-[(3-trifluoromethyl-phenylamino)-methyl]-[1,3,4]oxadiazol-2-yl}-heptyl)-formamide;
N-[(R)-2-(5-Benzyl-[1,3,4]oxadiazol-2-yl)-3-cyclopentyl-propyl]-N-hydroxyformamide;
N-Hydroxy-N-[(R)-2-(5-methyl-[1,3,4]oxadiazol-2-yl)-heptyl]-formamide; and
N-Hydroxy-N-((R)-2-{5-[2-(1H-indol-3-yl)-ethyl]-[1,3,4]oxadiazol-2-yl}-heptyl)-formamide; and pharmaceutically acceptable salts or solvates thereof.

6. A compound according to claim 5 selected from the group consisting of:
N-Hydroxy-[(R)-2-(5-phenylamino-[1,3,4]oxadiazol-2-yl)-heptyl]-formamide;
N-(5-{(R)-1-[(Formyl-hydroxy-amino)-methyl]-hexyl}-[1,3,4]oxadiazol-2-yl)-benzamide;
N-{(R)-2-[5-(Chloro-trifluoromethyl-phenylamino)-[1,3,4]oxadiazol-2-yl]-heptyl}-N-hydroxy-formamide;
N-Hydroxy-N-{(R)-2-[5-(methyl-phenyl-amino)-[1,3,4]oxadiazol-2-yl]-heptyl}-formamide;
Benzo[1,3]dioxole-5-carboxylic acid(5-{(R)-1-[(formyl-hydroxy-amino)-methyl]-hexyl}-[1,3,4]oxadiazol-1,2-yl)-amide;
N-{(R)-2-[5-(3,5-Dichloro-phenylamino)-[1,3,4]oxadiazol-2-yl]-heptyl}-N-hydroxy formamide;
N-[(S)-2-Fluoro-2-(5-phenylamino-[1,3,4]oxadiazol-2-yl)-heptyl]-N-hydroxy formamide; and
N-{(R)-2-[5-(2,3-Dihydro-benzo[1,4]dioxin-6-ylamino)-[1,3,4]oxadiazol-2-yl]-heptyl}-N-hydroxy-formamide; and pharmaceutically acceptable salts or solvates thereof.

7. A method of treating a bacterial infection by administering to a subject in need of such treatment a compound according to claim 1; or a pharmaceutically acceptable salt or solvate thereof.

8. A pharmaceutical composition comprising a compound according to claim 1, or a pharmaceutically acceptable salt or solvate thereof, and a pharmaceutically acceptable carrier.

* * * * *